United States Patent
Wu

(10) Patent No.: US 10,073,081 B2
(45) Date of Patent: Sep. 11, 2018

(54) MULTI-FUNCTION ALCOHOL TESTER

(71) Applicant: SHENZHEN JIESHIBO TECHNOLOGY CO., LTD., Shenzhen, Guangdong (CN)

(72) Inventor: Jianyong Wu, Guangdong (CN)

(73) Assignee: SHENZHEN JIESHIBO TECHNOLOGY CO., LTD., Shenzhen (CN)

(*) Notice: Subject to any disclaimer, the term of this patent is extended or adjusted under 35 U.S.C. 154(b) by 135 days.

(21) Appl. No.: 14/988,750

(22) Filed: Jan. 6, 2016

(65) Prior Publication Data
US 2017/0115273 A1    Apr. 27, 2017

(30) Foreign Application Priority Data
Oct. 27, 2015    (CN) .................... 2015 2 0837231 U

(51) Int. Cl.
*G01N 33/497* (2006.01)
(52) U.S. Cl.
CPC ................ *G01N 33/4972* (2013.01)
(58) Field of Classification Search
CPC ....... G01N 33/4972; H01M 4/75; H01R 4/48; H01R 13/7033
USPC ......................................... 73/23.3
See application file for complete search history.

(56) References Cited

U.S. PATENT DOCUMENTS

| | | | |
|---|---|---|---|
| 6,283,610 B1* | 9/2001 | Alajajian | F21L 4/04 362/102 |
| 6,837,095 B2* | 1/2005 | Sunshine | G01N 29/022 340/541 |
| 2005/0241871 A1* | 11/2005 | Stewart | G01N 33/4972 180/272 |
| 2007/0193335 A1* | 8/2007 | Son | G01N 33/497 73/23.3 |
| 2015/0165903 A1* | 6/2015 | Williams | B60K 28/063 701/36 |

FOREIGN PATENT DOCUMENTS

CN          104034870 A     *  9/2014

OTHER PUBLICATIONS

English translation of CN 104034870 A.*
YouTube—Alcohkit LongVersion Sub, accessed at https://www.youtube.com/watch?v=mteWOVMszXo, published on Feb. 2, 2015.*

* cited by examiner

*Primary Examiner* — Lisa Caputo
*Assistant Examiner* — Irving A Campbell

(57) ABSTRACT

The present application discloses a multi-function alcohol tester, including a housing, where the housing is internally provided with an alcohol test module, the alcohol test module includes a PCB mainboard, and the PCB mainboard is provided thereon with an alcohol measurement sensor communicating outside the housing; and the housing is further internally detachably connected with a function module, and the alcohol test module and the function module are powered by a battery disposed in the housing. The present application has advantages as follows: the multi-function alcohol tester has many functions, has a function module that can be detached or replaced, and is easy to carry.

7 Claims, 4 Drawing Sheets

MULTI-FUNCTION ALCOHOL TESTER

CROSS-REFERENCE TO RELATED APPLICATIONS

The present application claims the benefit of Chinese Patent Application No. 201520837231.8 filed on Oct. 27, 2015; the contents of which are hereby incorporated by reference.

BACKGROUND

Technical Field

The present application relates to alcohol testers, and in particular, to a multi-function alcohol tester that has many functions, has a function module that can be detached or replaced, and is easy to carry.

Related Art

With the rapid development of China's economy, people's living standards improve quickly, and more and more people have their own private cars. Drunk driving is a main factor that causes traffic accidents, and data shows that in major traffic accidents happening in China in recent years, nearly one third is caused by drunk driving. However, in people's communicative activities, drinking is inevitable, safe driving is feasible in the case of a relatively long time wait after a few drinks. How to determine a state of the human body so as to prevent motor vehicle drivers from drunk driving is also a requirement for life comfort and safety.

SUMMARY

To resolve the foregoing problem, an objective of the present application is to provide a multi-function alcohol tester that has many functions, has a function module that can be detached or replaced, and is easy to carry.

The present application is implemented by means of the following technical measures: A multi-function alcohol includes a housing, where the housing is internally provided with an alcohol test module, the alcohol test module includes a PCB mainboard, and the PCB mainboard is provided thereon with an alcohol measurement sensor communicating outside the housing; and the housing is further internally detachably connected with a function module, and the alcohol test module and the function module are powered by a battery disposed in the housing.

As one preferred example, the function module is slidably disposed in the housing, the housing is internally provided with positive and negative elastic pieces electrically connected with the battery, and the function module is electrically connected with the positive and negative elastic pieces when sliding in the housing.

As one preferred example, a round hole through which the alcohol measurement sensor extends out is disposed on an upper part of the housing, and the alcohol measurement sensor is sheathed with a decorating part.

As one preferred example, the PCB mainboard is provided thereon with an LED display screen, and a part of the housing corresponding to the LED display screen is set to be transparent.

As one preferred example, the housing includes a front inner shell and a rear inner shell combined with each other, and the front inner shell and the rear inner shell are respectively sheathed with a front outer shell and a rear outer shell after combined.

As one preferred example, a charging interface extending out of the housing is further disposed on a lower part of the PCB mainboard.

As one preferred example, the function module is one or more of an electric lighter, an LED lamp, an electric fan, an electronic cigarette, and a money detector.

As one preferred example, the electric lighter includes the positive and negative elastic pieces electrically connected with the battery and a heating piece slidably disposed in the housing, the heating piece is electrically connected with the positive and negative elastic pieces when sliding and extending out of the housing, and the heating piece is electrically insulated from the positive and negative elastic pieces when sliding and retracting into the housing.

As one preferred example, the heating piece is disposed on a heating piece holder, and the heating piece holder is connected with a connecting push rod and pushed by the connecting push rod to slide.

As one preferred example, the connecting push rod is connected with a spring that has one end fastened in the housing.

According to the present application, as the housing is further internally detachably connected with a function module, in addition to serving as an alcohol tester, the alcohol tester can also be used for some other functions (for example, used as an electric lighter, an LED lamp, an electric fan, an electronic cigarette, or a money detector) in other time, and can be simultaneously provided with multiple different function modules, so that replacement can be made to implement multiple functions. When an electric lighter module is mounted thereon, when a user takes a plane, the user may first dismount the electric lighter module and then mount it after landing, thereby avoiding the trouble that a lighter cannot be carried in the event of taking a plane. The present application has many functions, and has different functions that can be detached or replaced for use, and the present application is easy to carry and can conveniently detect whether alcohol content in the body is above the legal limit, so as to prevent motor vehicle drivers from drunk driving.

DETAILED DESCRIPTION

Figure 1:
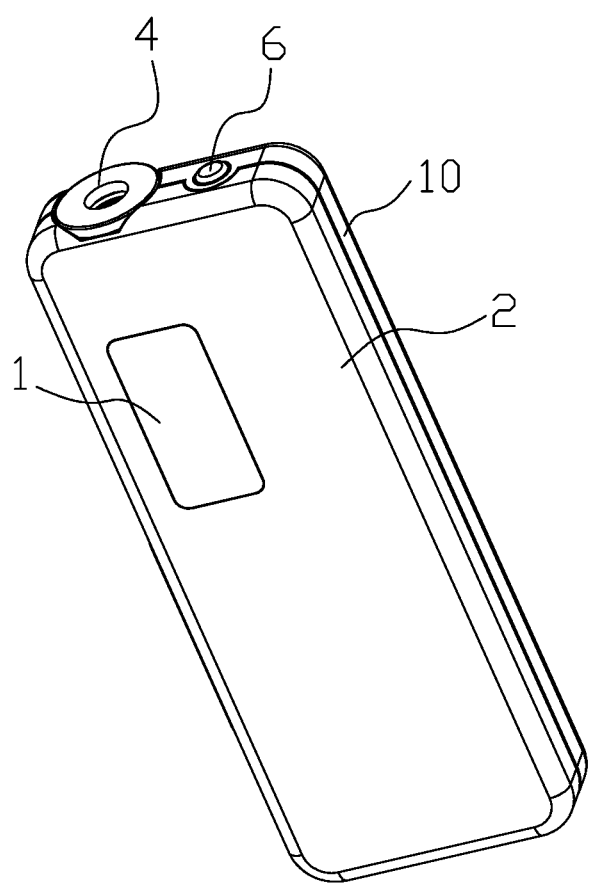
FIG. 1 is a schematic structural diagram according to an embodiment of the present application.

A multi-function alcohol tester of this embodiment, referring to FIG. 1 to FIG. 4, includes a housing, where the housing is internally provided with an alcohol test module, the alcohol test module includes a PCB mainboard 7, and the PCB mainboard 7 is provided thereon with an alcohol measurement sensor 5 communicating outside the housing; and the housing is further internally detachably connected with a function module, and the alcohol test module and the function module are powered by a battery 8 disposed in the housing.

In the alcohol tester, as the housing is further internally detachably connected with a function module, in addition to serving as an alcohol tester, the alcohol tester can also be used for some other functions (for example, used as an electric lighter, an LED lamp, an electric fan, an electronic cigarette, or a money detector) in other time, and can be simultaneously provided with multiple different function modules, so that replacement can be made to implement multiple functions. When an electric lighter module is mounted thereon, when a user takes a plane, the user may first dismount the electric lighter module and then mount it after landing, thereby avoiding the trouble that a lighter cannot be carried in the event of taking a plane. The product has many functions, and has different functions that can be detached or replaced for use, and the product is easy to carry and can conveniently detect whether alcohol content in the body is above the legal limit, so as to prevent motor vehicle drivers from drunk driving.

A multi-function alcohol tester of this embodiment, referring to FIG. 1 to FIG. 4, on the basis of the foregoing technical solution, may specifically be as follows: the function module is slidably disposed in the housing, the housing is internally provided with positive and negative elastic pieces 13 electrically connected with the battery 8, and the function module is electrically connected with the positive and negative elastic pieces 13 when sliding in the housing, so that the detachable function module is powered through the positive and negative elastic pieces 13.

A multi-function alcohol tester of this embodiment, referring to FIG. 1 to FIG. 4, on the basis of the foregoing technical solution, may specifically be as follows: a round hole air-blowing channel through which the alcohol measurement sensor 5 extends out is disposed on an upper part of the housing, and the alcohol measurement sensor 5 is sheathed with a decorating part 4.

A multi-function alcohol tester of this embodiment, referring to FIG. 1 to FIG. 4, on the basis of the foregoing technical solution, may specifically be as follows: the housing includes a front inner shell 3 and a rear inner shell 9 combined with each other, and the front inner shell 3 and the rear inner shell 9 are respectively sheathed with a front outer shell 2 and a rear outer shell 10 after combined, the PCB mainboard 7 is provided thereon with an LED display screen, and the front outer shell 2 is provided with a transparent LED cover plate 1 corresponding to the LED display screen 7. The front outer shell 2 and the rear outer shell 10 are all-metal made, thereby ensuring safety, fire prevention, abrasive resistance, solidity, and high level of the product.

Figure 2:
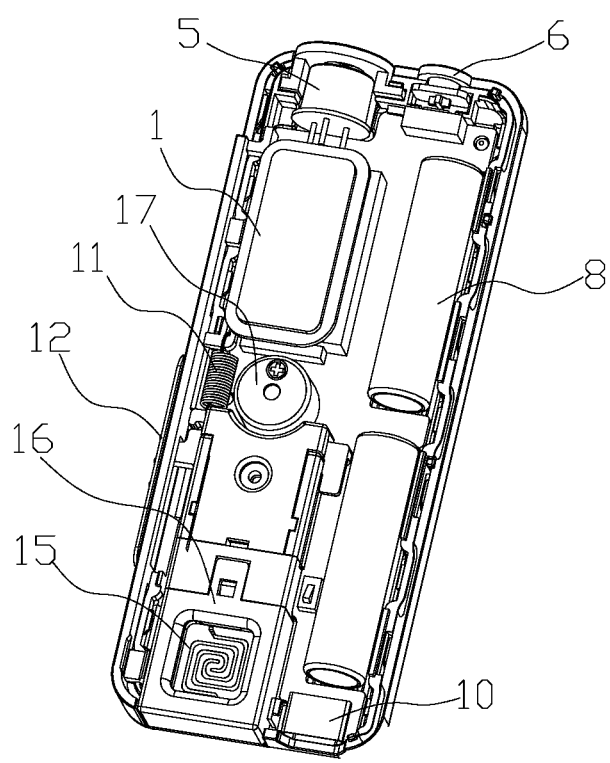
FIG. 2 is a schematic diagram of a structure whose housing is opened according to an embodiment of the present application.
Figure 3:
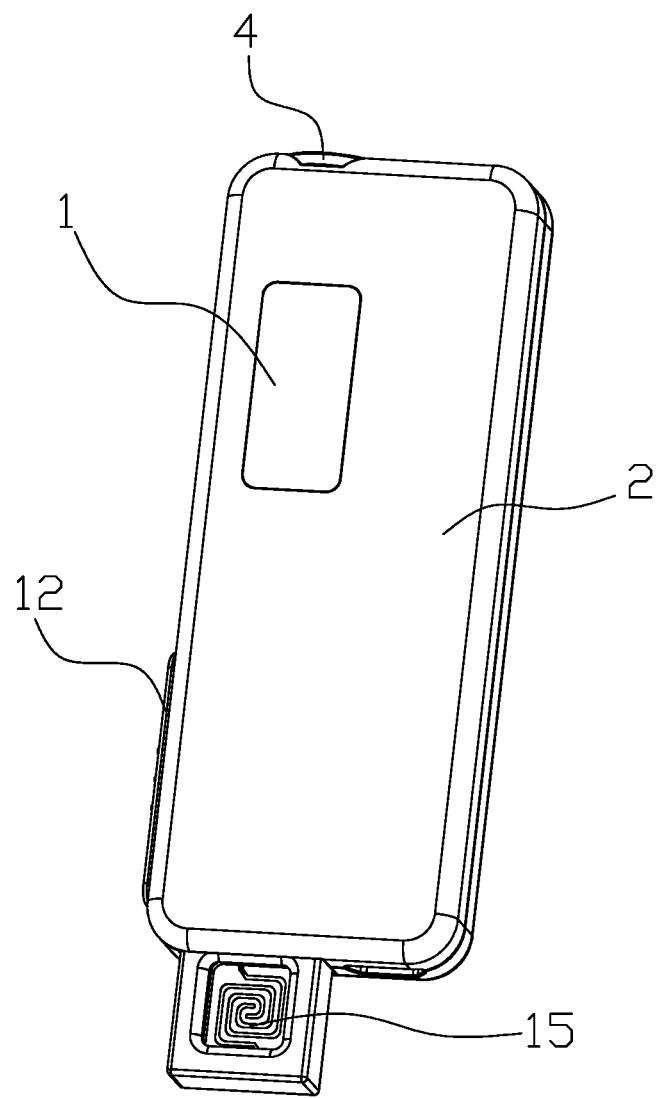
FIG. 3 is a schematic structural diagram of use of a lighter according to an embodiment of the present application.
Figure 4:
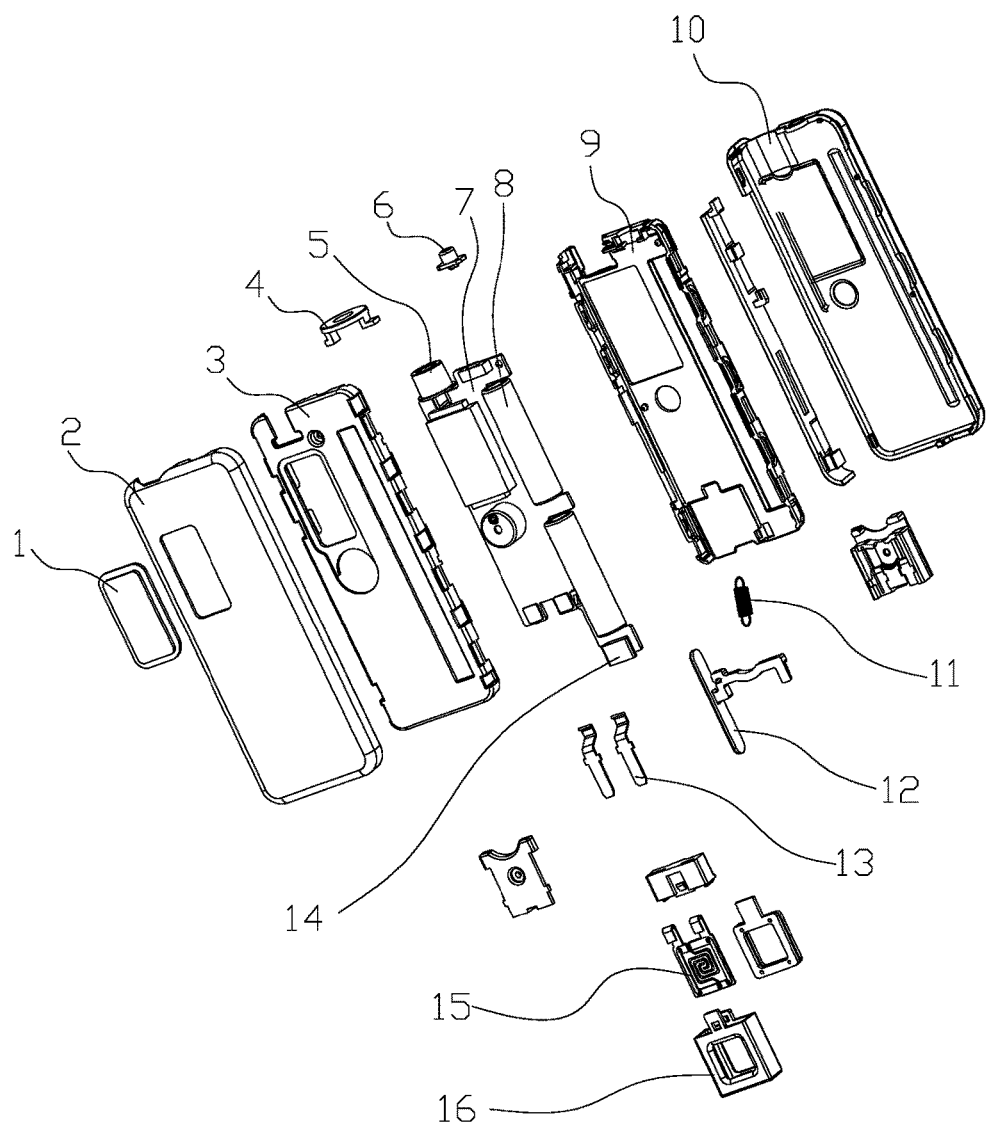
FIG. 4 is a schematic exploded structural diagram according to an embodiment of the present application.

A multi-function alcohol tester of this embodiment, referring to FIG. 2 to FIG. 4, on the basis of the foregoing technical solution, may specifically be as follows: a charging interface 14 extending out of the housing is further disposed on a lower part of the PCB mainboard 7.

A multi-function alcohol tester of this embodiment, referring to FIG. 1 to FIG. 4, on the basis of the foregoing technical solution, may specifically be as follows: the housing is further provided thereon with a key 6, used to turn on and off the tester, and the PCB mainboard 7 is further provided thereon with a buzzer 17, used to give an alarm prompt. The multi-function alcohol tester of this embodiment is further designed with prompt tones, and has two operation modes of silent and ringing, which meets requirements of different occasions and crowds (for example, the blind), and is easy to use.

As one preferred example, the lighter module includes the positive and negative elastic pieces electrically connected with the battery and a heating piece slidably disposed in the housing, the heating piece is electrically connected with the positive and negative elastic pieces when sliding and extending out of the housing, and the heating piece is electrically insulated from the positive and negative elastic pieces when sliding and retracting into the housing.

As one preferred example, the heating piece is disposed on a heating piece holder, and the heating piece holder is connected with a connecting push rod and pushed by the connecting push rod to slide.

As one preferred example, the connecting push rod is connected with a spring that has one end fastened in the housing.

A multi-function alcohol tester of this embodiment, referring to FIG. 2 to FIG. 4, when its function module is an electric lighter module, on the basis of the foregoing technical solution, may specifically be as follows: the electric lighter module includes the positive and negative elastic pieces 13 electrically connected with the battery 8 and a heating piece 15 slidably disposed in the housing, the heating piece 15 is electrically connected with the positive and negative elastic pieces 13 when sliding and extending out of the housing, and the heating piece 15 is electrically insulated from the positive and negative elastic pieces 13 when sliding and retracting into the housing. The heating piece 15 can be used as a lighter when sliding and extending out of the housing.

A multi-function alcohol tester of this embodiment, referring to FIG. 2 to FIG. 4, on the basis of the foregoing technical solution, may specifically be as follows: the heating piece part 15 and the heating piece holder 16 are dismounted together, which is suitable for some special occasions, for example, occasions such as planes on which lighters are forbidden.

A multi-function alcohol tester of this embodiment, referring to FIG. 2 to FIG. 4, on the basis of the foregoing technical solution, may specifically be as follows: the heating piece 15 is disposed on the heating piece holder 16, the heating piece holder 16 is connected with a connecting push rod 12 and pushed by the connecting push rod 12 to slide, and the connecting push rod 12 is connected with a spring 11 that has one end fastened in the housing, thereby helping the heating piece holder 16 to slide back.

The above describes the alcohol tester of the present application and is used to help understand the present application, but embodiments of the present application are not limited to the foregoing embodiments, and any change, modification, replacement, combination and simplification made without departing from the principle of the present application should be equivalent substitution manners and should be encompassed in the protection scope of the present application.

What is claimed is:

1. A multi-function alcohol tester, comprising: a housing, wherein the housing is internally provided with an alcohol test module, the alcohol test module comprises a PCB mainboard, and the PCB mainboard is provided thereon with an alcohol measurement sensor communicating outside the housing; and the housing is further internally detachably connected with a function module, and the alcohol test module and the function module are powered by a battery disposed in the housing;

wherein the function module is slidably disposed in the housing, the housing is internally provided with positive and negative elastic pieces electrically connected with the battery, and the function module is electrically connected with the positive and negative elastic pieces when sliding in the housing;

wherein the function module comprises an electric lighter; and wherein the electric lighter comprises the positive and negative elastic pieces electrically connected with the battery and a heating piece slidably disposed in the housing, the heating piece is electrically connected with the positive and negative elastic pieces when sliding and extending out of the housing, and the heating piece is electrically insulated from the positive and negative elastic pieces when sliding and retracting into the housing.

2. The multi-function alcohol tester according to claim 1, wherein the alcohol measurement sensor is sheathed with a decorating part.

3. The multi-function alcohol tester according to claim 1, wherein the PCB mainboard is provided thereon with an LED display screen, and a part of the housing corresponding to the LED display screen is set to be transparent.

4. The multi-function alcohol tester according to claim 1, wherein the housing comprises a front inner shell and a rear inner shell combined with each other, and the front inner shell and the rear inner shell are respectively sheathed with a front outer shell and a rear outer shell after combined.

5. The multi-function alcohol tester according to claim 1, wherein a charging interface extending out of the housing is further disposed on a lower part of the PCB mainboard.

6. The multi-function alcohol tester according to claim 1, wherein the heating piece is disposed on a heating piece holder, and the heating piece holder is connected with a connecting push rod and pushed by the connecting push rod to slide.

7. The multi-function alcohol tester according to claim 6, wherein the connecting push rod is connected with a spring that has one end fastened in the housing.

* * * * *